United States Patent [19]  [11] 4,405,823
Maki et al. [45] Sep. 20, 1983

[54] PROCESS FOR THE PRODUCTION OF PHENOLS

[75] Inventors: Takao Maki, Fujisawa; Tetsuo Masuyama, Machida; Toshiharu Yokoyama, Yokohama, all of Japan

[73] Assignee: Mitsubishi Chemical Industries Limited, Tokyo, Japan

[21] Appl. No.: 411,122

[22] Filed: Aug. 24, 1982

[30] Foreign Application Priority Data

Aug. 24, 1981 [JP] Japan ................................ 56-132481
Oct. 7, 1981 [JP] Japan ................................ 56-159716
Nov. 5, 1981 [JP] Japan ................................ 56-177582

[51] Int. Cl.$^3$ ............................................. C07C 37/56
[52] U.S. Cl. ..................................................... 568/801
[58] Field of Search ........................................ 568/801

[56] References Cited

U.S. PATENT DOCUMENTS 3,379,774 4/1963 Forni ................................... 568/801
3,929,911 12/1975 von Dierendonck et al. ..... 568/801

FOREIGN PATENT DOCUMENTS 2820394 11/1978 Fed. Rep. of Germany ...... 568/801
1015077 12/1965 United Kingdom ................ 568/801

Primary Examiner—Werren B. Lone
Attorney, Agent, or Firm—Sughrue, Mion, Zinn, Macpeak and Seas

[57] ABSTRACT

A process for producing phenols from benzenemonocarboxylic acids, or their salts, esters, or anhydrides is described, comprising contacting these starting materials with molecular oxygen-containing gas and steam in a liquid phase in the presence of a copper compound, a manganese compound, and a rare earth element compound. This process can be performed either by a one-step reaction method or by a two-step reaction method. In accordance with the present process, the formation of by-products such as high boiling by-products or diphenyl ethers is inhibited and the selectivity of phenols can be greatly increased.

10 Claims, No Drawings

PROCESS FOR THE PRODUCTION OF PHENOLS

FIELD OF THE INVENTION

The present invention relates to a process for the production of phenols and, more particularly, to a process for the production of phenols in which a copper compound/manganese compound/rare earth element compound system is used as a catalyst for the oxidative decarboxylation of benzenemonocarboxylic acid, or their salts, esters, or acid anhydrides in a liquid phase.

BACKGROUND OF THE INVENTION

It is known that in a process for producing phenyl benzoate or its hydrolytic product, phenol, by the oxidative decarboxylation of benzenemonocarboxylic acid, or its salt, ester, or acid anhydride, a copper compound is used as a catalyst. It is also known that addition of a magnesium compound to the copper compound permits selective production of phenyl benzoate and its hydrolytic product, phenol. The use of such catalyst systems, however, results in the formation of large amounts of high boiling by-products, giving rise to serious problems in that the rate of formation of phenol is reduced with a lapse of time and the recovery of catalyst is reduced. Therefore, in order to increase the selectivity of phenol, various improvements in catalyst have been made. U.S. Pat. No. 3,379,774 discloses that the use of a three component catalyst of copper, magnesium, and manganese increases the rate of formation of phenol and reduces the amount of high boiling point product (pitch) being formed. U.S. Pat. No. 3,637,807 discloses that a copper/manganese catalyst produces large amounts of phenoxybenzoic acid and diphenyl ether, and controls the formation of pitch. British Pat. No. 1,015,077 (corresponding to U.S. Pat. No. 3,277,184) describes that a copper/rare earth element cation catalyst increases the rate of formation of phenol.

A method is also known in which benzenemonocarboxylic acids, or their salts, esters, or acid anhydrides are used as starting materials, and in which the starting material is contacted with molecular oxygen-containing gas in the presence of a catalyst at a first step to form mainly benzenemonocarboxylic acid phenyl esters, and the esters are hydrolyzed at a second step to obtain phenols (see U.S. Pat. No. 3,929,911). This method is called a "two-step reaction method". It is said that the two-step reaction method is an energy-saving process whereby the amount of steam used in the hydrolysis reaction can be markedly saved compared with a one-step reaction method in which the oxidation reaction and the hydrolysis reaction are performed at the same time in the same reactor. However, when the above-described known catalysts are used in the two-step reaction method, large amounts of high boiling point by-products are formed as is the case with the one-step reaction method, resulting in a reduction in yield. This presents problems in that the rate of formation of phenol is lowered with a lapse of time and the recovery of catalyst is reduced.

SUMMARY OF THE INVENTION

As a result of extensive investigations, it has now been found that the use of a copper compound/manganese compound/at least one rare earth element compound catalyst enables to inhibit the formation of high boiling by-products or diphenyl ethers, and to greatly increase the selectivity of phenols.

The present invention, therefore, relates to a process for producing phenols which comprises contacting benzenemonocarboxylic acids, or their salts, esters, or acid anhydrides with molecular oxygen-containing gas in a liquid phase in the presence of a copper compound/manganese compound/rare earth element compound catalyst.

DETAILED DESCRIPTION OF THE INVENTION

The copper compound, manganese compound, and rare earth element compound as used herein must be soluble in a reaction mixture under the reaction conditions employed.

Copper compounds which can be used include copper oxides, carboxylic acid salts, carbonic acid salts, and hydroxides, such as copper benzoate, cuprous oxide, cupric oxide, and copper salicylate. Manganese compounds which can be used include oxides and carboxylic acid salts, such as manganese benzoate, and manganese (II) or (III) oxide. Rare earth element compounds which can be used include compounds of each of rare earth elements from lanthanum (La) having an atomic number of 57 to lutetium (Lu) having an atomic number of 71 as well as yttrium (Y) and scandium (Sc). In particular, compounds of each of lanthanum (La), cerium (Ce), praseodymium (Pr), neodymium (Nd), promethium (Pm), and samarium (Sm) are preferred. As lanthanum compounds, commercial didymium compounds containing a neodymium compound, a praseodymium compound, a samarium compound, etc., can be used. In addition, soluble rare earth element compounds, such as benzoic acid salts, carboxylic acid salts, e.g., acetic acid salts, and oxides, and those compounds which are converted into compounds soluble in a reaction mixture under reaction conditions can be used. These rare earth element compounds can be used singly or in combination with each other.

The amount of the copper compound used is, as calculated as copper, from 0.01 to 5% by weight, preferably from 0.1 to 3% by weight, based on the starting material. The amount of the manganese compound used is, as calculated as manganese, from 0.01 to 10% by weight, preferably from 0.1 to 5% by weight, based on the starting material. The amount of the rare earth element compound used is, as calculated as a rare earth element, from 0.01 to 10% by weight, preferably from 0.1 to 5% by weight, based on the starting material.

The molar ratio of each catalyst used is Cu/Mn/rare earth element compound=1/0.1–10/0.1–10, preferably 1/1–4/1–4, calculated as a metal. Further, the molar ratios of Mn/Cu≧1, rare earth element compound/Cu≧1 and rare earth element compound=0.5–2 are preferred.

Benzenemonocarboxylic acids which can be used are benzoic acid and its substituted derivatives. In the case of substituted benzoic acid derivatives, it is required that at least one of the adjacent positions (ortho positions) of the carboxyl group is vacant. Substituents include an alkyl group, a halogen atom, etc., which are inert to the oxidation behavior of copper. In more detail, o-toluic acid, m-toluic acid, p-toluic acid, m-chlorobenzoic acid, p-chlorobenzoic acid, p-methoxybenzoic acid, p-phenylbenzoic acid, etc., can be used.

It is most preferred from an economical viewpoint that the molecular oxygen-containing gas as used herein is air. In addition, oxygen-riched air, air diluted with nitrogen, and a mixed gas of oxygen and nitrogen or carbon dioxide in any desired ratio can be used. As is well known, the molecular oxygen-containing gas is used to oxidize cuprous salts into cupric salts in a reaction zone.

Production of phenols can be performed by the following methods:

(1) Benzenemonocarboxylic acids, or their salts, esters, or acid anhydrides, are contacted with a mixture of molecular oxygen-containing gas and steam in the presence of a copper compound, a manganese compound, and a rare earth element compound in a single reaction zone to obtain phenols (this method is hereinafter referred to as a "one-step reaction method"); and (2) Benzenemonocarboxylic acids, or their salts, esters, or acid anhydrides, are contacted with molecular oxygen-containing gas in the presence of a copper compound, a manganese compound, and a rare earth element compound in a first reaction zone to form mainly benzenemonocarboxylic acid phenyl esters, and the phenyl esters are contacted with steam in the presence of a copper compound, a manganese compound, and a rare earth element compound in a second reaction zone to achieve hydrolysis of the phenyl esters and obtain phenols (this method is hereinafter referred to as a "two-step reaction method").

The benzenemonocarboxylic acid phenyl esters formed in the first reaction zone in the above two-step reaction method are intermediates for the production of phenols, which themselves are not the desired products of the invention.

It is believed that the reaction mechanism of the one-step reaction method is substantially the same as that of the two-step reaction method. That is, it is believed that benzenemonocarboxylic acid phenyl esters are first formed as intermediates and, thereafter, they are successively hydrolyzed by steam into phenols.

As can be seen from the above-described reaction mechanism, in the one-step reaction method, a mixture composed mainly of phenols and containing benzenemonocarboxylic acid phenyl esters is obtained. In this case, when the relative amount of steam in the reaction zone is large, the proportion of phenols in the mixture is increased, whereas when it is small, the proportion of the esters is increased.

The one-step reaction method and the two-step reaction method will hereinafter be explained in detail.

One-Step Reaction Method

In accordance with the one-step reaction method, molecular oxygen-containing gas and steam are intermittently or continuously blown into a molten mixed mass of starting material and catalyst charged to a stirring type vessel reactor, a bubble column reactor or the like, under the conditions of temperature of from 180° to 300° C., preferably from 200° to 250° C. and pressure of from 0.1 to 10 atmospheric pressures, preferably from 1 to 3 atmospheric pressures. It is preferred that steam is blown after being heated to the reaction temperature or temperatures higher than the reaction temperature.

When the molecular oxygen-containing gas and steam are continuously blown, the flow rate of the molecular oxygen-containing gas is, as calculated as oxygen gas, from 0.01 to 100 l/hr (NTP), preferably from 0.1 to 20 l/hr (NTP), and the flow rate of steam is from 0.01 to 100 g/hr, preferably from 0.1 to 20 g/hr, both being per mmole of copper.

The reaction time is preferably from about 0.1 to 10 hours although it varies depending on the amount of the catalyst used, the reaction temperature, the reaction pressure, etc. If desired, an inert solvent can be used in the reaction.

Phenols formed are generally recovered by distillation. Unreacted benzoic acids are separated from the catalyst and reaction product by known techniques such as distillation and reused as starting materials. As is the case with the benzoic acids, the catalyst is separated by known separation techniques and reused. When the catalyst is inevitably entrained in high boiling point by-products, etc., and removed from the reaction system, a fresh catalyst is supplemented.

Two-Step Reaction Method

At the first step, molecular oxygen-containing gas is intermittently or continuously blown into a molten starting material and a catalyst dissolved therein charged into a stirring type vessel reactor, a bubble column reactor or the like, under the conditions of temperature of from 180° to 300° C., preferably from 200° to 250° C., and pressure of from 0.1 to 10 atmospheric pressure, preferably from 1 to 3 atmospheric pressure to effect a gas-liquid contact. The amount of the molecular oxygen-containing gas being blown is, as calculated as oxygen gas per millimole of copper, from 0.01 to 100 l/hr (NTP) and preferably from 0.1 to 20 l/hr (NTP). The reaction time is preferably from about 0.1 to 5 hours although it varies depending on the amount of the catalyst used, the reaction temperature, the reaction pressure, etc. The reaction at the first step is carried out without blowing steam from the outside of the reaction system.

At the second step of the present two-step reaction method, hydrolysis is carried out under the same conditions as or slightly moderate conditions compared with the oxidation reaction at the first step in any of temperature, pressure, and reaction mode. At the second step, steam is blown into the reaction system from the outside thereof. The amount of steam being blown into the reaction system is from 0.01 to 100 g/hr, preferably from 0.1 to 30 g/hr, per millimole of copper. It is preferred for the steam to be blown into the reaction system after being preliminarily heated to the same temperature as or higher temperatures than the reaction temperature. It is also preferred that oxygen-containing gas is blown into the reaction system along with steam. The amount of oxygen-containing gas being blown in combination with steam is, as calculated as oxygen gas per millimole of copper, from 0.1 ml/hr (NTP) to 10 l/hr (NTP) and preferably from 0.01 to 1 l/hr (NTP). The reaction time is preferably from about 0.1 to 5 hours although it varies depending on conditions such as the amount of the catalyst used, the reaction temperature, and the reaction pressure. In both of the oxidation reaction at the first step and the hydrolysis reaction at the second step, if desired, a solvent inert to the reaction can be used.

Phenols obtained by the two-step reaction method is generally recovered by distillation. Unreacted benzenemonocarboxylic acids are separated from the catalyst and reaction products by known techniques such as distillation, and reused as starting materials. As is the case with the unreacted starting material, the catalyst is separated and recovered by known separation techniques, and reused. It is preferred to employ a method of recovering by extracting with water, a method of recovering by burning, etc. The catalyst recovered by such methods can be reused without any reduction in activity. When the catalyst is inevitably entrained in high boiling point by-products, etc., and removed from the reaction system, a fresh catalyst is supplemented.

Some of the major advantages obtained by the process of the invention, which could not be expected for the conventional methods, are shown below:

(1) In particular, phenols can be produced with very high selectivity by the use of the catalyst of the invention.

(2) On the contrary, the formation of diphenyl ethers and high boiling point products, i.e., tar components, is inhibited and, therefore, a reduction in the rate of formation of phenols is maintained at a markedly low level.

(3) Since the amount of tar formed is small, the separation of the catalyst from the residue is easy and the loss of the catalyst is reduced, which is prefered from an economical standpoint.

Although the function of each component of the catalyst of the invention is not clear at present, it is assumed as follows:

A copper compound plays a significant role in the catalyst of the invention and is present as copper (II) benzenemonocarboxylate during the reaction, whereas a manganese compound and a rare earth element compound serve to be an auxiliary component. For example, when the manganese compound alone is added to the main catalyst component, copper compound, although the rate of formation of phenols is increased at earlier stages of the reaction, it gradually drops and considerable amount of diphenyl ethers are formed. On the other hand, if the manganese compound is added in combination with the rare earth element compound, the formation of diphenyl ethers is minimum and phenols are formed stably over a long period of time. The reason for this is that the rare earth element compound prevents the excessive oxidation reaction by the manganese and acts to maintain the manganese in the preferred atomic valency state, presumably in the divalent or trivalent state, as a result of which the copper, manganese and rare earth element form a stable reaction state.

The following examples are given to illustrate the invention in greater detail although the invention is not limited thereto.

Examples 1 to 10 and Comparative Examples 1 to 7 are concerned with the one-step reaction method, and Examples 11 to 13 and Comparative Example 3-1, with the two-step reaction method. Examples 14 to 15 and Comparative Example 9 are directed to the recovery of catalyst.

Furthermore, conversion and selectivity of various compounds and aromatic ring balance were calculated as follows:

BA Conversion (mol %) =

$$\frac{BA \text{ Charged (mmol)} - BA \text{ Recovered (mmol)}}{BA \text{ Charged (mmol)}} \times 100$$

PHL Selectivity (mol %) =

$$\frac{PHL \text{ Formed (mmol)}}{BA \text{ Charged (mmol)} - BA \text{ Recovered (mmol)}} \times 100$$

Total PHL Selectivity (mol %) =

$$\frac{PHL \text{ Formed (mmol)} + PHBA \text{ (mmol)}}{BA \text{ Charged (mmol)} - BA \text{ Recovered (mol)} - PHBA \text{ Formed (mmol)}} \times 100$$

DPE Selectivity (mol %) =

$$\frac{DPE \text{ Formed (mmol)} \times 2}{BA \text{ Charged (mmol)} - BA \text{ Recovered (mmol)}} \times 100$$

Middle Boiling By-Products Selectivity (mol %) =

$$\frac{\begin{array}{c}SA \text{ (mmol)} + \Sigma HOBA \text{ (mmol)} + \\ 2 \times \Sigma POBA \text{ (mmol)} + 2 \times \Sigma BOBA \text{ (mmol)} + \\ 2 \times DPE \text{ (mmol)}\end{array}}{BA \text{ Charged (mmol)} - BA \text{ Recovered (mmol)}} \times 100$$

Aromatic Ring Balance (mol %) =

$$\frac{\begin{array}{c}PHL \text{ (mmol)} + 2 \times PHBA \text{ (mmol)} + \\ SA \text{ (mmol)} + \Sigma HOBA \text{ (mmol)} + 2 \times DPE \text{ (mmol)} + \\ 2 \times \Sigma POBA \text{ (mmol)} + 2 \times \Sigma BOBA \text{ (mmol)} + \\ \text{Formed Tar (mg/94.1)}\end{array}}{BA \text{ Charged (mmol)}} \times 100$$

BA: Benzoic acid
PHL: Phenol
PHBA: Phenyl benzoate
DPE: Diphenyl ether
HOBA: m- and p-Hydroxybenzoic acid
POBA: o-, m- and p-Phenoxybenzoic acid
BOBA: m- and p-Benzoyloxybenzoic acid
SA: Salicyclic acid
$\Sigma$: Total of isomers

EXAMPLE 1

A four-necked separation type cylindrical glass reactor having an inner diameter of 31 mm and a height of 210 mm was charged with 134.7 g (1,103.2 mmol) of benzoic acid, 1.61 g (6.4 mmol) of basic copper carbonate ($CuCO_3 \cdot Cu(OH)_2 \cdot H_2O$), 1.82 g (25.6 mmol) of manganese oxide (MnO), and 4.17 g (12.8 mmol) of lanthanum oxide ($La_2O_3$). A gas introduction inlet and a distillation column were connected to the reactor, and the temperature was raised to 235° C. After the temperature reached 235° C., heated air and steam were blown into the molten benzoic acid from the bottom of the reactor at flow rates of 15 l/hr (NTP) and 30 g/hr, respectively, to start the reaction. During the reaction, the reaction mass was stirred at a rate of 270 (rpm) by the use of a screw type stirring blade.

A gas component and a low boiling liquid component containing phenol were separated by distillation in the distillation column (a Vigreaux type tube having an inner diameter of 30 mm and a height of 300 mm) and recovered in a liquid trap. The distillation column was maintained at 110° to 140° C. At three hour intervals during the reaction, fresh benzoic acid was supplied in an amount corresponding to the total weight of phenol, benzoic acid, etc., recovered in the liquid trap. The liquid recovered in the liquid trap was diluted with 1,4-dioxane and analyzed by liquid chromatography. The amounts of phenol collected 3 hours, 6 hours, 9 hours, and 12 hours after the start of the reaction were 5.32 g, 7.29 g, 7.52 g, and 8.17 g, respectively, and the amounts of benzoic acid collected were 5.23 g, 4.97 g, 4.53 g, and 3.63 g, respectively. The amounts of benzoic acid replenished 3 hours, 6 hours, and 9 hours after the start of the reaction were 13.0 g, 15.0 g, and 20.0 g, respectively.

12 Hours after the start of the reaction, the reaction was stopped, and the reaction solution remaining in the reactor was diluted with 1,4-dioxane and analyzed by liquid chromatography. The reaction solution contained 118.1 g of benzoic acid, 1.2 g of phenol, and 3.5 g of phenyl benzoate.

From 182.7 g (1,496.3 mmol) of benzoic acid charged were obtained 29.5 g (313.9 mmol) of phenyl and 3.5 g (17.5 mmol) of phenyl benzoate. The amount of unreacted benzoic acid was 136.4 g (1,117.4 mmol). The benzoic acid conversion, the free phenol selectivity, and the total phenol selectivity, as determined by the formulae as described hereinbefore, were 25.3%, 82.9%, and 91.7%, respectively. The formation of diphenyl ether was not observed.

COMPARATIVE EXAMPLE 1

The procedure of Example 1 was repeated wherein the lanthanum oxide was excluded from the catalyst system.

The amounts of phenol in the distillates 3 hours, 6 hours, 9 hours and 12 hours after the start of the reaction were 5.2 g, 7.2 g, 8.0 g and 7.9 g, respectively, and the amounts of benzoic acid, 3.5 g, 3.8 g, 4.4 g and 4.2 g, respectively. The amounts of benzoic acid replenished 3 hours, 6 hours and 9 hours after the start of the reaction were 14 g, 14 g and 14 g, respectively. The reaction solution remaining in the reactor contained 0.8 g of phenol, 109.2 g of benzoic acid, 5.7 g of phenyl benzoate, and 1.4 g of diphenyl ether. The reaction results are shown in Table 1.

EXAMPLE 2

Cu-Mn-La Catalyst

In this example, there was used the same catalyst as in Example 1 except that the amount of lanthanum oxide was changed to 2.09 g (6.4 mmol). Using the catalyst, the procedure of Example 1 was repeated wherein the reaction time was 6 hours and no benzoic acid was replenished in the course of reaction. The results are shown in Table 1.

COMPARATIVE EXAMPLE 2

Cu-Mn-Mg Catalyst

The procedure of Example 2 was repeated wherein 1.03 g of magnesium oxide was used in place of lanthanum oxide. The results are shown in Table 1.

COMPARATIVE EXAMPLE 3

Cu-Mg Catalyst

The procedure of Example 2 was repeated wherein manganese oxide was not used. The results are shown in Table 1.

EXAMPLE 3

The procedure of Example 2 was repeated wherein 7.43 g (25.6 mmol as La) of didymium oxide ($La_2O_3$: 56.3%, $Nd_2O_3$: 33.0%, $Pr_6O_{11}$: 8.8%, $Sm_2O_3$: 1.5%) was used in place of lanthanum oxide. The results are shown in Table 1.

TABLE 1

| | Catalyst | Reaction Time (hr) | Benzoic Acid Conversion (%) | Selectivity PHL (%) | Selectivity Total PHL (%) | DPE (%) |
|---|---|---|---|---|---|---|
| Example 1 | Cu—Mn—La | 12 | 25.3 | 82.9 | 91.7 | — |
| Comparative Example 1 | Cu—Mn | 12 | 30.4 | 71.1 | 83.8 | 3.6 |
| Example 2 | Cu—Mn—La | 6 | 19.1 | 78.3 | 92.0 | — |
| Comparative Example 2 | Cu—Mg—Mn | 6 | 21.5 | 68.9 | 81.3 | — |
| Comparative Example 3 | Cu—La | 6 | 17.4 | 73.8 | 85.5 | — |
| Example 3 | Cu—Mn—didymium | 6 | 14.2 | 86.1 | 100 | — |

EXAMPLE 4

A 300 ml four-necked rotary stirring type round bottom flask equipped with 3 baffle plates (5 mm×40 mm) and a stirring blade with 20 mm diameter made of teflon was charged with 134.7 g (1,103.2 mmol) of benzoic acid, 1.61 g (6.4 mmol) of basic copper carbonate ($CuCO_3 \cdot Cu(OH)_2 \cdot H_2O$), 1.82 g (25.6 mmol) of manganese oxide (MnO), and 4.17 g (12.8 mmol) of lanthanum oxide ($La_2O_3$). A gas introduction inlet and a distillation column were connected to the reactor, which was then heated by the use of a heating mantle. After the temperature reached 235° C., 30 l/hr (NTP) of heated air and 30 g/hr of steam were blown into the molten benzoic acid from the bottom of the reactor to start the reaction. The stirring rate was 1,300 (rpm).

A gas component and a low boiling liquid component containing phenol were separated by distillation in the same manner as in Example 1.

After 135 minutes from the start of the reaction, the reaction was stopped. The reaction solution remaining in the reactor and the effluent were each diluted with 1,4-dioxane to 500 ml. A 10 ml portion of each of the residual solution and the effluent was taken and analyzed by liquid chromatography to determine phenol (PHL), benzoic acid (BA), and phenyl benzoate (PHBA). For the residual solution, middle boiling point by-products were quantitatively analyzed and the amount of tar formed was measured. The quantitative analysis was performed as follows:

A 10 ml portion of the 1,4-dioxane diluted solution was distilled at a kettle temperature of 110° to 130° C. to remove the 1,4-dioxane, and the residue was then cooled to ordinary temperature. To the residue were added 20 ml of diethyl ether and 20 ml of 2 N hydrochloric acid. After a shaking extraction procedure was fully performed, an aqueous layer was withdrawn, and an ether layer, after methylated with diazomethane, was quantitatively analyzed by gas chromatography.

Middle boiling point by-products detected include salicylic acid (SA), m- and p-hydroxybenzoic acid (HOBA), o-, m- and p-phenoxybenzoic acid (POBA), m- and p-benzoyloxybenzoic acid (BOBA), and diphenyl ether (DPE). These compounds were quantitatively analyzed by determining a correction factor for each compound.

The amount of tar was measured by the following method:

A 100 ml portion of the above-obtained diluted 1,4-dioxane solution was taken, from which the 1,4-dioxane was distilled away by heating at a kettle temperature of 110° to 130° C. The residue was cooled to ordinary temperature, and 200 ml of diethyl ether and 200 ml of 2 N hydrochloric acid were added thereto. After a shaking extraction procedure was fully performed, an aqueous layer was withdrawn. Then, 100 ml of an aqueous saturated solution of sodium hydrogencarbonate was added to an ether layer, and the resulting mixture was fully subjected to an extraction procedure to extract acidic substances such as benzoic acid. This procedure was repeated once more. The ether layer was then filtered, and the residue remaining on the filter was fully washed with diethyl ether and dried. Thereafter, the amount of the residue was measured and indicated as the amount of tar.

The analytical results are as follows:

The distillate contained 19.36 g (205.7 mmol) of PHL, 13.75 g (112.6 mmol) of BA, and 0.26 g (1.3 mmol) of PHBA. In the solution remaining in the reactor, there were 0.93 g (9.9 mmol) of PHL, 82.56 g (176.1 mmol) of BA, 8.03 g (40.5 mmol) of PHBA, 0.11 g (0.83 mmol) of SA, 0.04 g (0.3 mmol) of m-HOBA, 0.51 g (2.4 mmol) of o-POBA, 0.05 g (0.21 mmol) of m-POBA, 0.01 (0.06 mmol) of p-POBA, 0.56 g (2.16 mmol) of m- and p-BOBA, and 0.16 g (calculated as PHL) of tar. The benzoic acid conversion, the selectivity of each of phenol, total phenol (phenol+phenyl benzoate formed), middle boiling point by-products, and tar, and the aromatic ring balance are shown in Table 2.

EXAMPLE 5

The procedure of Example 4 was repeated wherein the amount of air blown was 15 l/hr (NTP) and the reaction time was 180 minutes. The results are shown in Table 2.

COMPARATIVE EXAMPLE 4

The procedure of Example 4 was repeated wherein a catalyst consisting of 1.61 g (6.4 mmol) of basic copper carbonate ($CuCO_3 \cdot Cu(OH)_2 \cdot H_2O$) and 2.06 g (51.2 mmol) of magnesium oxide (MgO) was used and the reaction time was 130 minutes. The results are shown in Table 2.

COMPARATIVE EXAMPLE 5

The procedure of Comparative Example 4 was repeated wherein the amount of air blown was 15 l/hr (NTP) and the reaction time was 190 microns. The results are shown in Table 2.

It can be seen from the results shown in Tables 1 and 2 that the process of the invention is markedly superior to the conventional method utilizing the Cu-Mg catalyst in that, in particular, the total phenol selectivity is very high and the tar selectivity is very low.

EXAMPLE 6

A four-necked separable cylindrical glass reactor having an inner diameter of 31 mm and a height of 210 mm was charged with 134.7 g (1,103.2 mmol) of benzoic acid, 1.61 g (6.4 mmol) of basic copper carbonate ($CuCO_3 \cdot Cu(OH)_2 \cdot H_2O$), 1.82 g (25.6 mmol) of manganese oxide (MnO), and 8.58 g (25.6 mmol) of cerium acetate. A gas introduction inlet and a distillation column were connected to the reactor, which was then heated by the use of an electric furnace. After the temperature reached 235° C., 15 l/hr (NTP) of heated air and 30 g/hr of steam were blown into the molten benzoic acid from the bottom of the reactor to start the reaction.

A gas component and a low boiling component containing phenol were separated by distillation in the same manner as in Example 1.

After 6 hours from the start of the reaction, the reaction was stopped. A reaction solution remaining in the reactor and a distillate were each diluted with 1,4-dioxane and analyzed by liquid chromatography.

The amounts of benzoic acid, phenol and phenyl benzoate contained in the solution remaining in the reactor were 105.1 g, 0.5 g, and 1.7 g, respectively. The amounts of benzoic acid and phenol in the distillate were 4.4 g and 16.1 g, respectively. From 134.7 g of the charged benzoic acid were obtained 16.6 g (176.1 mmol) of phenol and 1.7 g (8.6 mmol) of phenyl benzoate, and the amount of unreacted benzoic acid was 109.5 g (897.3 mmol).

The formation of phenoxybenzoic acid was hardly observed. The conversion, the phenol selectivity, etc., are shown in Table 3.

EXAMPLE 7

The procedure of Example 6 was repeated wherein 2.89 g (12.8 mmol) of yttrium oxide ($Y_2O_3$) was used in place of cerium acetate. The results are shown in Table 3.

EXAMPLE 8

The procedure of Example 6 was repeated wherein 4.76 g (6.4 mmol) of terbium oxide ($Tb_4O_7$) was used in place of cerium acetate. The results are shown in Table 3.

TABLE 2

| | Catalyst | Amount of Air l/Hr (NTP) | Reaction Time (min) | BA Conversion (%) | Selectivity | | | | Aromatic Ring Balance (%) |
| --- | --- | --- | --- | --- | --- | --- | --- | --- | --- |
| | | | | | PHL (%) | Total PHL (%) | Middle Boiling By-Products (%) | Tar (%) | |
| Example 4 | Cu—Mn—La (1:2:2) | 30 | 135 | 28.5 | 68.6 | 94.4 | 3.4 | 0.5 | 99.7 |
| Example 5 | Cu—Mn—La (1:2:2) | 15 | 180 | 22.9 | 77.8 | 93.6 | 3.8 | 0.4 | 99.6 |
| Comparative Example 4 | Cu—Mg (1:4) | 30 | 130 | 23.4 | 37.4 | 80.1 | 6.6 | 3.5 | 98.3 |
| Comparative Example 5 | Cu—Mg (1:4) | 15 | 190 | 27.3 | 69.5 | 84.8 | 6.5 | 2.9 | 98.6 |

EXAMPLE 9

The procedure of Example 6 was repeated wherein 3.23 g (9.6 mmol) of neodymium oxide ($Nd_2O_3$) was used in place of cerium acetate.

The amounts of benzoic acid, phenol and phenyl benzoate contained in the residual solution were 101.6 g, 1.6 g and 3.2 g, respectively. The amounts of benzoic acid and phenol contained in the distillate were 7.4 g and 13.8 g, respectively. From 134.7 g of the charged benzoic acid were obtained 15.4 g (163.7 mmol) of phenol and 3.3 g (16.5 mmol) of phenyl benzoate, and the amount of unreacted benzoic acid was 109.1 g (893.5 mmol). Almost no phenoxybenzoic acid was observed. The conversion, the phenol selectivity, etc., are shown in Table 3.

EXAMPLE 10

The procedure of Example 6 was repeated wherein 4.36 g (4.27 mmol) of praseodymium oxide ($Pr_6O_{11}$) was used in place of cerium acetate. The results are shown in Table 3.

COMPARATIVE EXAMPLE 6

The procedure of Example 6 was repeated wherein cerium acetate was not used. The results are shown in Table 3.

COMPARATIVE EXAMPLE 7

The procedure of Example 6 was repeated wherein 1.03 g (25.6 mmol) of magnesium oxide was used in place of cerium acetate and 2.02 g (12.8 mmol) of dimanganese trioxide was used in place of manganese oxide. The results are shown in Table 3.

TABLE 3

| | Catalyst | Benzoic Acid Conversion (%) | Selectivity PHL (%) | Selectivity Total PHL (%) | Amount of Phenoxybenzoic Acid Formed |
|---|---|---|---|---|---|
| Example 6 | Cu—Mn—Ce | 18.7 | 85.5 | 93.6 | + |
| Example 7 | Cu—Mn—Y | 17.2 | 84.6 | 93.3 | ++ |
| Example 8 | Cu—Mn—Tb | 18.1 | 85.0 | 93.4 | ++ |
| Example 9 | Cu—Mn—Nd | 19.0 | 78.0 | 93.8 | + |
| Example 10 | Cu—Mn—Pr | 16.1 | 78.8 | 98.8 | + |
| Comparative Example 6 | Cu—Mn | 23.4 | 80.3 | 92.5 | +++ |
| Comparative Example 7 | Cu—Mn—Mg | 21.5 | 68.9 | 81.3 | +++ |

EXAMPLE 11

A 300 ml four-necked rotary stirring type round bottom glass reactor equipped with 3 baffle plates (5 mm × 40 mm) and a stirring blade with 20 mm diameter made of teflon was charged with 134.7 kg (1,103.2 mmol) of benzoic acid, 1.61 g (6.4 mmol) of basic copper carbonate ($CuCO_3 \cdot Cu(OH)_2 \cdot H_2O$), 1.82 g (25.6 mmol) of manganese oxide (MnO), and 4.17 g (12.3 mmol) of lanthanum oxide ($La_2O_3$). A gas introduction inlet and a distillation column were connected to the reactor which was then heated by a heating mantle. After the temperature reached 235° C., heated air was blown into molten benzoic acid from the bottom of the reactor at a flow rate of 30 l/hr (NTP) to start an oxidation reaction at a first reaction step. The stirring rate was 1,300 (rpm).

A gas component and a low boiling liquid component containing phenol were separated by distillation in the same manner as in Example 1.

After 100 minutes from the start of the reaction, the reaction was stopped and, thereafter, 0.788 g of the solution in the reactor and the distillate collected in the liquid trap were taken out. The solution and the distillate were each diluted with 1,4-dioxane and analyzed by liquid chromatography. Liquid chromatographic analysis indicated that the solution contained in the reactor contained 0.4% by weight of phenol (PHL), 53.3% by weight of benzoic acid (BA), and 37.3% by weight of phenyl benzoate (PHBA), and that the distillate consisted of 6.7 g (71.2 mmol) of PHL, 1.51 g (12.3 mmol) of BA, and 0.04 g (0.2 mmol) of PHBA.

After the first oxidation reaction step was stopped, the reaction solution was lowered in temperature while blowing air thereinto. After the temperature reached 200° C., 30 g/hr of steam and 0.3 l/hr (NTP) of heated air were blown into the reactor from the bottom thereof to start a hydrolysis reaction as a second step. The stirring rate was 1,300 (rpm). The reaction was stopped 120 minutes after the start thereof.

The residual solution in the reactor and the distillate were diluted with 1,4-dioxane to a predetermined volume of 500 ml respectively. A 10 ml portion of each of the residual solution and the distillate was taken out and analyzed by liquid chromatography to determine the amounts of PHL, BA, and PHBA. For the residual solution, quantitative analysis of middle boiling point by-products and the measurement of the amount of tar were performed in the same way as in Example 4.

The analytical results were as follows:

The distillate contained 11.09 g (117.8 mmol) of PHL and 0.73 g (6.0 mmol) of BA. In the residual solution in the reactor, there were observed 5.29 g (56.2 mmol) of PHL, 81.52 g (667.7 mmol) of BA, 14.3 g (72.4 mmol) of PHBA, 0.3 g (2.2 mmol) of m-HOBA, 0.6 g (2.8 mmol) of o-POBA, 0.35 g (1.4 mmol) of m- and p-BOBA, and 0.29 g (3.1 mmol, as calculated as PHL) of tar. The benzoic acid conversion (mol%), the selectivity (mol%) of each of phenol, total phenol (formed phenol + formed phenylbenzoic acid), middle boiling point by-products, and tar, and the aromatic ring balance (mol%) are shown in Table 4.

EXAMPLE 12

The procedure of Example 11 was repeated wherein 8.58 g (25.6 mmol) of cerium acetate ($Ce(CH_3COO)_3 \cdot H_2O$) was used in place of lanthanum oxide. The results are shown in Table 3.

EXAMPLE 13

The procedure of Example 11 was repeated wherein 4.17 g of didymium oxide (56.3% $La_2O_3$, 33.0% $Nd_2O_3$, 8.8% $Pr_6O_{11}$, 1.5% $Sm_2O_3$) was used in place of lanthanum oxide. The results are shown in Table 4.

COMPARATIVE EXAMPLE 8

The procedure of Example 11 was repeated wherein 2.06 g (51.2 mmol) of magnesium oxide was used in addition to basic copper carbonate as a catalyst. The results are shown in Table 4.

TABLE 4

|  | Example 11 | Example 12 | Example 13 | Comparative Example 8 |
|---|---|---|---|---|
| Catalyst (molar ratio) | Cu—Mn—La (1:2:2) | Cu—Mn—Ce (1:2:2) | Cu—Mn—Didymium (1:2:2) | Cu—Mg (1:4) |
| Benzoic Acid Conversion (mol %) | 37.5 | 38.4 | 37.8 | 41.2 |
| Selectivity (mol %) | | | | |
| Phenol | 59.7 | 63.2 | 60.5 | 57.4 |
| Total Phenol | 93.9 | 89.1 | 93.2 | 70.5 |
| Middle Boiling By-Products | 2.6 | 3.1 | 2.8 | 3.9 |
| Tar | 0.8 | 0.7 | 0.9 | 4.1 |
| Aromatic Ring Balance (mol %) | 99.4 | 97.5 | 99.3 | 92.1 |

As apparent from the results shown in Table 4, the process of the invention is superior to the conventional process utilizing a Cu-Mg catalyst in that, in particular, the total phenol selectivity is very high, and the formation of tar is markedly reduced.

EXAMPLE 14

A 300 ml four-necked round bottom rotary stirring type glass reactor equipped with three baffle plates (5 mm × 40 mm) and a stirring blade with 20 mm diameter made of teflon was charged with 134.7 g (1,103.2 mmol) of benzoic acid, 1.61 g (6.4 mmol) of basic copper carbonate ($CuCO_3 \cdot Cu(OH)_2 \cdot H_2O$), 1.82 g (25.6 mmol) of manganese oxide, and 4.17 g of didymium oxide (56.3% $La_2O_3$, 33.0% $Nd_2O_3$, 8.8% $Pr_6O_{11}$, 1.5% $Sm_2O_3$). A gas inlet and a distillation column were connected to the reactor which was then heated by a heating mantle. After the temperature reached 235° C., 30 l/hr (NTP) of heated air and 30 g/hr or steam were blown into molten benzoic acid from the bottom of the reactor to start a reaction. The stirring rate was 1,300 (rpm).

A gas component and a low boiling liquid component containing phenol were separated by distillation in the same manner as in Example 1.

The reaction was stopped 135 minutes after the start thereof. The residual solution in the reactor and the distillate were each diluted with 1,4-dioxane to 500 ml.

A 10 ml sample was withdrawn, and phenol (PHL), benzoic acid (BA), and phenyl benzoate (PHBA) were quantitatively analyzed by liquid chromatography. For the residual solution, the quantitative analysis of the middle boiling by-products and the measurement of the amount of tar formed were performed in the same manner as in Example 4.

The analytical results are as follows:

The distillate contained 17.24 g (183.2 mmol) of PHL and 4.48 g (36.7 mmol) of BA. In the residual solution in the reactor, there were contained 1.53 g (16.3 mmol) of PHL, 92.63 g (758.6 mmol) of BA, 10.85 g (53.2 mmol) of PHBA, 0.12 g (0.88 mmol) of SA, 0.65 g (30 mmol) of o-POBA, 0.71 g (2.8 mmol) of (mtp)-BOBA, and 0.16 g (1.6 mmol, as calculated as PHL). The conversion, the selectivity, and the aromatic ring balance are shown in Table 5.

From the residual solution diluted with 1,4-dioxane were distilled away 1,4-dioxane, benzoic acid, etc., to obtain a solid residue. The solid residue was placed in a reaction tube made of quartz having an inner diameter of 30 mm, and burned at 500° C. for 3 hours while passing air therethrough. The burned product was black powder. To the black powder were added basic copper carbonate, manganese oxide, and didymium oxide in amounts corresponding to those lost in the previous analysis. Using the resulting mixture, the same procedure as above was performed. The analytical results are shown in Table 5. The procedure was further repeated and the analytical results are also shown in Table 5. These results demonstrate the possibility of the catalyst being reused by burning.

EXAMPLE 15

The procedure of Example 14 was repeated wherein a four-necked separable cylindrical glass reactor having an inner diameter of 31 mm and a height of 210 mm was used, 4.17 g (12.8 mmol) of lanthanum oxide ($La_2O_3$) was used in place of commercial didymium oxide, heated air was blown at a flow rate of 15 l/hr (NTP), and the reaction time was set to 6 hours. The results are shown in Table 6.

COMPARATIVE EXAMPLE 9

The procedure of Example 15 was performed wherein lanthanum oxide was not added. The results demonstrate that the PHL selectivity is seriously reduced, i.e., the rate of hydrolysis of PHBA is lowered.

TABLE 5

|  | Example 14 | | |
|---|---|---|---|
| Catalyst | Cu—Mn—Didymium | | |
| Number of Reactions Repeated | 1 | 2 | 3 |
| Benzoic Acid Conversion (%) | 29.6 | 28.3 | 28.6 |
| Selectivity (%) | | | |
| PHL | 61.1 | 62.8 | 59.8 |
| Total PHL | 92.5 | 94.3 | 92.0 |
| Middle Boiling By-Products | 4.3 | 3.7 | 4.4 |
| Tar | 0.5 | 0.9 | 0.8 |
| Aromatic Ring Balance (%) | 99.4 | 99.9 | 99.5 |

TABLE 6

|  | Example 15 | | | | Comparative Example 9 | |
|---|---|---|---|---|---|---|
| Catalyst | Cu—Mn—La | | | | Cu—Mn | |
| Number of Repeated Reaction | 1 | 2 | 3 | 4 | 1 | 2 |
| Benzoic Acid Conversion (%) | 17.4 | 16.7 | 19.2 | 18.4 | 23.4 | 21.6 |
| Selectivity (%) | | | | | | |
| PHL | 70.9 | 76.3 | 72.9 | 75.5 | 80.3 | 61.2 |
| Total PHL | 89.1 | 93.3 | 88.9 | 89.7 | 92.5 | 91.0 |

While the invention has been described in detail and with reference to specific embodiments thereof, it will be apparent to one skilled in the art that various changes and modifications can be made therein without departing from the spirit and scope thereof.

What is claimed is:

1. A process for producing phenols which comprises contacting benzenemonocarboxylic acids, or their salts, esters, or acid anhydrides with molecular oxygen-containing gas and steam in a liquid phase at a temperature of from 180° to 300° C. and a pressure of from 0.1 to 10 atmospheric pressure in the presence of a copper compound, a manganese compound, and a rare earth element compound.

2. The process as claimed in claim 1, wherein the molecular oxygen-containing gas is air.

3. The process as claimed in claim 1, wherein the rare earth element is a lanthanum, didymium, cerium, neodymium, praseodymium, promethium, or samarium compound.

4. The process as claimed in claim 1, wherein the benzenemonocarboxylic acids, or their salts, esters or acid anhydrides are contacted with molecular oxygen-containing gas and steam at the same time in a single reaction zone.

5. The process as claimed in claim 1, wherein the benzenemonocarboxylic acids or their salts, esters, or acid anhydrides are contacted with molecular oxygen-containing gas in the presence of a copper compound, a manganese compound, and a rare earth element compound in a first reaction zone to form mainly benzenemonocarboxylic acid phenyl ester, and the benzenemonocarboxylic acid phenyl ester is then contacted with steam in a second reaction zone to hydrolyze it whereby phenols are obtained.

6. The process as claimed in claim 1, wherein the benzenemonocarboxylic acid feed is molten benzoic acid.

7. The process as claimed in claim 1, wherein the amounts of the copper compound, manganese compound and rare earth element compounds are 0.01 to 5% by weight, 0.01 to 10% by weight and 0.01 to 10% by weight, respectively, based on the weight of the starting benzenemonocarboxylic acids or salts, esters or anhydrides thereof.

8. The process a claimed in claim 7, wherein the molar ratios of the copper compound:manganese compound:rare earth element compound are, calculated as metal, Cu/Mn/rare earth element=1/0.1–10/0.1–10.

9. The process as claimed in claim 7, wherein the amounts of the copper compound, manganese compound and rare earth element compound are 0.1 to 3% by weight, 0.1 to 5% by weight and 0.1 to 5% by weight, respectively, based on the weight of the starting benzenemonocarboxylic acids or salts, esters or anhydrides thereof.

10. The process as claimed in claim 8, wherein the molar ratios of the copper compound:manganese compound:rare earth element compound are, calculated as a metal, Cu/Mn/rare earth element=1/1–4/1–4.

* * * * *